(12) United States Patent
Sato et al.

(10) Patent No.: US 7,547,808 B2
(45) Date of Patent: Jun. 16, 2009

(54) PROCESS FOR PRODUCING ALDEHYDE WITH 2-POSITION BRANCHED LONG-CHAIN ALKYL

(75) Inventors: Haruhito Sato, Chiba (JP); Takashi Kashiwamura, Chiba (JP); Yoshio Ikeda, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 60 days.

(21) Appl. No.: 11/912,895

(22) PCT Filed: Jul. 21, 2006

(86) PCT No.: PCT/JP2006/314529

§ 371 (c)(1),
(2), (4) Date: Oct. 29, 2007

(87) PCT Pub. No.: WO2007/013379

PCT Pub. Date: Feb. 1, 2007

(65) Prior Publication Data

US 2009/0076311 A1    Mar. 19, 2009

(30) Foreign Application Priority Data

Jul. 25, 2005   (JP)   ............... 2005-214678

(51) Int. Cl.
*C07C 45/55* (2006.01)
(52) U.S. Cl. ..................... 568/483
(58) Field of Classification Search ........... 568/483
See application file for complete search history.

(56) References Cited

U.S. PATENT DOCUMENTS 3,558,716 A   1/1971   Engelhardt et al.
7,402,610 B2 *  7/2008   Sato et al. ............ 514/558

FOREIGN PATENT DOCUMENTS

JP   03-090042   4/1991
JP   2004-256404   9/2004
JP   2004-331561   11/2004

OTHER PUBLICATIONS

Badger, Alison M. et al., "Antiarthritic and Suppressor Cell Inducing Activity of Azaspiranes: Structure-Function Relationships of a Novel Class of Immunomodulatory Agents", J. Med. Chem., vol. 33, pp. 2963-2970, 1990.

\* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

To provide a process capable of producing an aldehyde with a 2-position branched long-chain alkyl with high yield and high selectivity. The process for producing an aldehyde with a 2-position branched long-chain alkyl represented by the following general formula (2) contains: using a 2-position branched epoxide represented by the following general formula (1) as a raw material; and subjecting the epoxide to acid rearrangement reaction with a polyacid of a metallic oxoacid as a catalyst. In the formulae, n represents an integer of from 5 to 17.

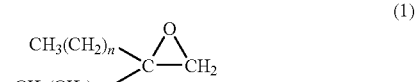

(1)

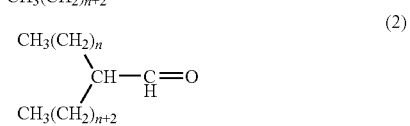

(2)

5 Claims, 3 Drawing Sheets

PROCESS FOR PRODUCING ALDEHYDE WITH 2-POSITION BRANCHED LONG-CHAIN ALKYL

TECHNICAL FIELD

The present invention relates to a process for producing an aldehyde with a 2-position branched long-chain alkyl suitable for an intermediate raw material used in production of a branched alcohol, a branched fatty acid, an aliphatic amine and the like, a resin raw material, such as 1,3-alkanediol and a bisphenol derivative, and a raw material of a functional chemical utilizing a Schiff base and the like.

BACKGROUND ART

A process for industrially producing a 2-position branched alcohol (such as 2-octyl-1-dodecanol) by applying so-called Guerbet reaction to a higher alcohol (such as 1-decanol) has been conventionally known. However, only one report has been made for a technique for producing a 2-position branched aldehyde (see Patent Document 1). According to Patent Document 1, in the case where a branched saturated aldehyde is produced by utilizing Guerbet reaction, a branched alcohol and a branched unsaturated aldehyde are present as mixtures, and thus it is expected that it is difficult to produce a branched saturated aldehyde with high purity. Patent Document 1 disclosed in Example 2 that the amount of a hydrogenation catalyst is necessarily added in an amount of 7% by mass for improving the yield of the branched aldehyde, but when the ratio of the hydrogenation catalyst is decreased, such a problem and the like arise in that a branched alcohol is produced as the major product.

An aldehyde with a 2-position branched long-chain alkyl can be produced through dimerization of a higher alcohol utilizing Guerbet reaction, but the production process is not practical since the activity per unit catalyst is significantly low.

Acid rearrangement reaction of a 1,2-epoxide of an α-olefin provides various rearrangement products (which include aldehydes, and also include ketones and unsaturated alcohols), and thus a 1,2-epoxide is utilized only for production of a 1,2-diol through hydration reaction or production of a polyester polyol through addition reaction with a dibasic carboxylic acid. It has been reported that acid rearrangement of a 1,2-epoxide in a 1,4-dioxane solvent provides a linear aldehyde (see, for example, Patent Document 2). However, an aldehyde with a 2-position branched long-chain alkyl cannot be produced by the production method using an epoxide of an α-olefin.

Patent Document 1: U.S. Pat. No. 3,558,716

Patent Document 2: JP-A-2004-256404

DISCLOSURE OF THE INVENTION

Problems to be Solved by the Invention

The present invention has been made under the aforementioned circumstances, and an object thereof is to provide a method capable of producing an aldehyde with a 2-position branched long-chain alkyl with high yield and high selectivity.

Means for Solving the Problems

As a result of earnest investigations made by the present inventors, it has been found that by subjecting a 2-position branched epoxide to acid rearrangement reaction using a polyacid of a metallic oxoacid as a catalyst, an aldehyde with a 2-position branched long-chain alkyl can be produced with high yield and high selectivity, and the aldehyde with a 2-position branched long-chain alkyl as a target product can be obtained at a high concentration with a considerably high activity per unit catalyst, whereby such operations as separation of the catalyst and purification can be simplified. The invention has been completed based on the findings.

The invention provides a process for producing an aldehyde with a 2-position branched long-chain alkyl shown below.

1. A process for producing an aldehyde with a 2-position branched long-chain alkyl represented by the following general formula (2) containing: using a 2-position branched epoxide represented by the following general formula (1) as a raw material; and subjecting the epoxide to acid rearrangement reaction with a polyacid of a metallic oxoacid as a catalyst.

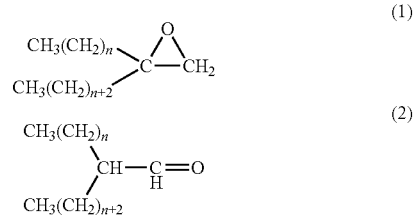

(In the Formulae, N Represents an Integer of from 5 to 17.)

2. The process for producing an aldehyde with a 2-position branched long-chain alkyl as described in the item 1, wherein the 2-position branched epoxide is an epoxidized product of a vinylidene olefin obtained by dimerizing an α-olefin in the presence of a metallocene complex catalyst.

3. The process for producing an aldehyde with a 2-position branched long-chain alkyl as described in the item 1 or 2, wherein in the general formulae (1) and (2), n represents an integer of from 7 to 9.

4. The process for producing an aldehyde with a 2-position branched long-chain alkyl as described in one of the items 1 to 3, wherein the polyacid of a metallic oxoacid is a polyacid containing tungstic acid, molybdic acid or vanadic acid.

5. The process for producing an aldehyde with a 2-position branched long-chain alkyl as described in the item 4, wherein the polyacid containing tungstic acid, molybdic acid or vanadic acid is an isopolyacid that is a polyacid of tungstic acid, molybdic acid or vanadic acid, or a heteropolyacid that is a polyacid of tungstic acid, molybdic acid or vanadic acid with phosphoric acid, silicic acid or boric acid.

Advantage of the Invention

In the present invention, by subjecting a 2-position branched epoxide to acid rearrangement reaction using a polyacid of a metallic oxoacid as a catalyst, an aldehyde with a 2-position branched long-chain alkyl can be produced with high yield and high selectivity, and the aldehyde with a 2-position branched long-chain alkyl as a target product can be obtained at a high concentration with a considerably high activity per unit catalyst, whereby such operations as separation of the catalyst and purification can be simplified.

BEST MODE FOR CARRYING OUT THE INVENTION

Figure 1:
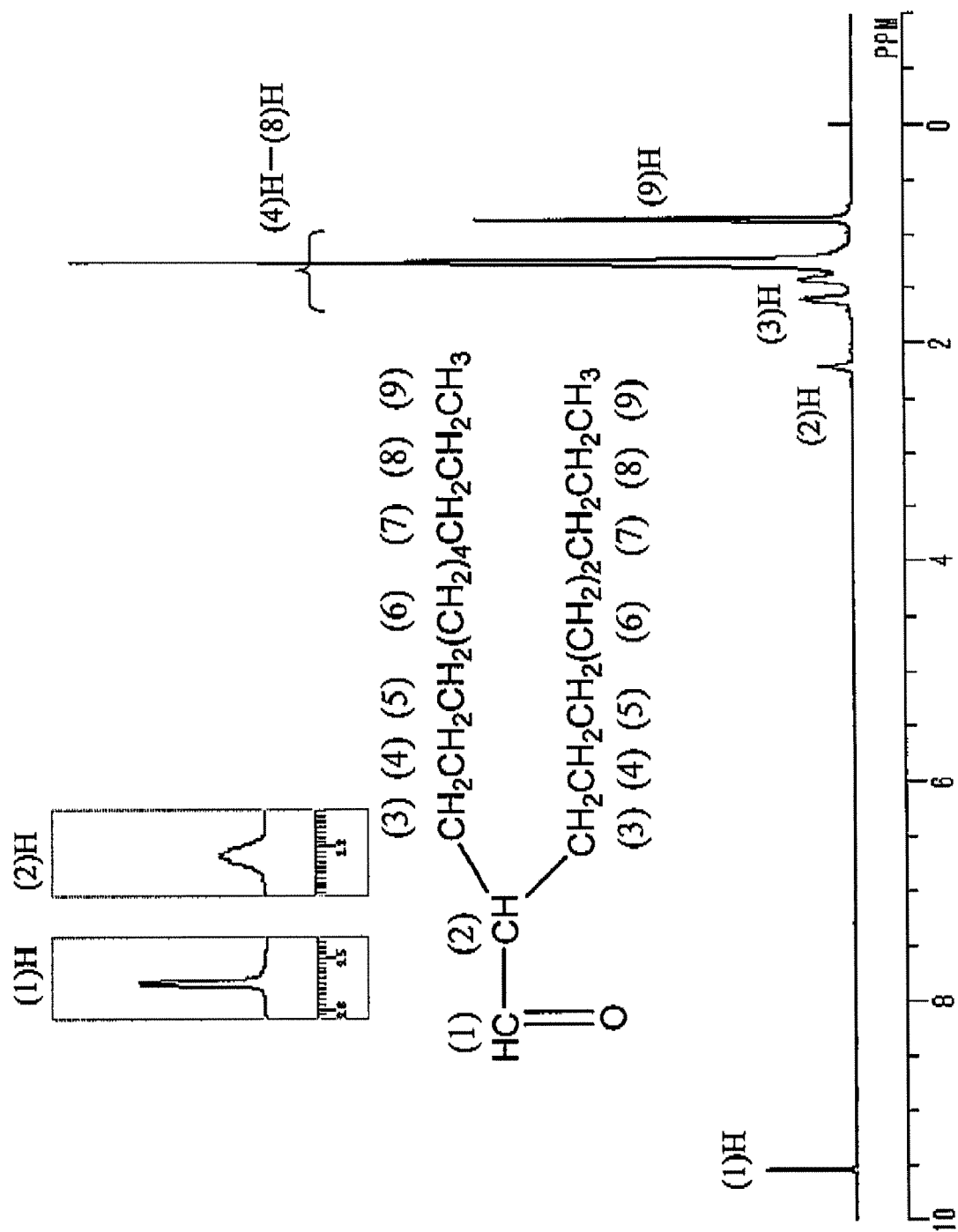
FIG. 1 The figure shows a $^1$H-NMR spectrum of 2-octyl-1-dodecanal obtained in Example 1.

The 2-position branched epoxide represented by the general formula (1) used as a raw material in the present invention can be obtained, for example, by epoxidizing a vinylidene olefin (general formula (4)) obtained by dimerizing an α-olefin (general formula (3)) in the presence of a metallocene complex catalyst, as shown by the following reaction pathway. By using the 2-position branched epoxide (general formula (1)) as a raw material, the epoxide is subjected to acid rearrangement reaction using a polyacid of a metallic oxoacid, whereby the aldehyde with a 2-position branched long-chain alkyl (general formula (2)) is produced.

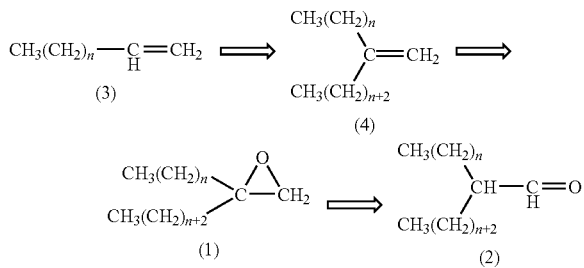

(In the Formulae, N Represents an Integer of from 5 to 17, and Preferably from 7 to 9.)

In the acid rearrangement reaction, a long-chain alkyl 2-position branched unsaturated alcohol represented by the following general formula (i), a long-chain alkyl 2-position branched 1,2-diol represented by the following general formula (ii), and an epoxide dimer represented by the following general formula (iii) are formed as by-products.

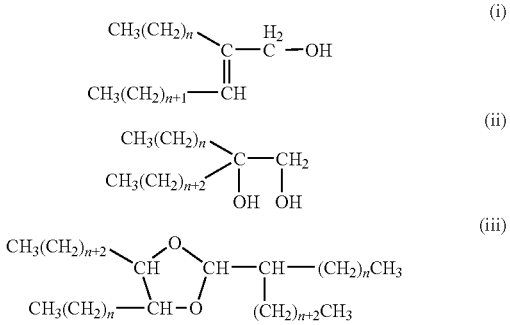

(In the Formulae, N has the Same Meaning as Above.)

Examples of the metallocene complex catalyst used for dimerization of the α-olefin include a catalyst containing a metallocene complex and an organoaluminum compound, and a catalyst containing a metallocene complex and a borate (an ionization agent of the complex). A transition metal complex of Group 4 of the Periodic Table having a conjugated 5-membered carbocyclic structure as a ligand is used as the metallocene complex, and alkylaluminoxane or a group of compounds having an alkyl group and metallic aluminum bonded directly, such as trialkyl aluminum, is used as the organoaluminum compound.

Examples of the α-olefin represented by the general formula (3) include 1-octene, 1-decene, 1-dodecene, 1-tetradecene, 1-hexadecene, 1-octadecene and 1-eicocene.

The metallocene complex includes a complex of a metal of Group 4 of the Periodic Table having a conjugated 5-membered carbocyclic structure, such as zirconocene dichloride, bis(dimethylcyclopentadienyl) zirconium dichloride, bis(indenyl)zirconium dichloride and bis(tetrahydroindenyl)zirconium dichloride, a metallic complex obtained by replacing zirconium in the metallic complex with titanium or hafnium, and a metallic complex obtained by replacing the chloride thereof with an alkyl group, a 1,3-diketone, a β-ketoester or trifluoromethane sulfonate.

Examples of the organoaluminum compound include alkylaluminoxane, such as methylaluminoxane and isobutylaluminoxane, and an alkylaluminum compound, such as triethylaluminum, triisobutylaluminum and trioctylaluminum.

Examples of the borate include a dimethylanilinium salt of tetrakis(pentafluorophenyl)borate, trityl tetrakis(pentafluorophenyl)borate, trimethylammonium tetrakis(pentafluorophenyl)borate, benzylpyridinium tetrakis(pentafluorophenyl)borate and trityl tetraphenylborate.

The dimerization reaction of the α-olefin can be carried out, for example, in such a manner that the catalyst and the α-olefin are sequentially added to a hydrocarbon solvent (such as benzene, toluene, xylene, pentane and hexane) and stirred at a temperature of 50° C. or lower for about 24 hours, and after completing the reaction, and the catalyst is deactivated with hydrochloric acid, followed by distilling the product in vacuum, and a dimer of the α-olefin can be obtained with high purity and high yield.

In the case where a metallocene complex catalyst containing a metallocene complex and alkylaluminoxane, preferably methylaluminoxane, is used, the charging ratio (molar ratio) of the complex metal and Al of the alkylaluminoxane is important. In the case where the ratio is in a range of from 1.0 to 0.01, the yield on dimerization is good, and the vinylidene olefin content in the dimer is increased. In the case where it is 1.0 or less, the yield on dimerization per unit complex is increased, and in the case where it is 0.01 or more, a trimer and higher oligomers are suppressed from being formed, whereby the yield of the dimer is improved. The reaction temperature is about from room temperature to 100° C. In the case where it is room temperature or higher, the dimerization reaction is accelerated, and in the case where it is 100° C. or lower, the complex is suppressed from being deactivated, whereby the yield of the dimer is improved. The charging ratio (proportion) of the metallocene complex with respect to the α-olefin is generally about from 1 to 1,000 μmol of the metallocene complex per 1 mol of the α-olefin. In the case where the amount of the metallocene complex is 1 μmol or more, the dimerization reaction is accelerated, and in the case where it is 1,000 μmol or less, heat generation is suppressed to facilitate control of the reaction.

A dimer containing the vinylidene olefin at a high concentration can also be produced in the case of using the metallocene complex catalyst containing a metallocene complex and a borate. With the metallocene complex catalyst containing a metallocene complex and a borate, an organoaluminum compound, preferably trialkylaluminum, and more preferably triisobutylaluminum, is preferably used in combination.

The using amount of the borate is preferably in a range of from a substantially equal amount to five times the amount of the complex metal in terms of molar number. The addition amount of the organoaluminum is not particularly limited, and is preferably at least such a molar number that is capable of being reacted with impurities, such as water, hydroxyl groups and amines coexisting in the reaction system. The reaction temperature is about from room temperature to 150° C., and the optimum temperature is at around 100° C. The addition ratio of the metallocene complex to the α-olefin is the same as that in the case using the metallocene complex catalyst containing a metallocene complex and methylaluminoxane described above.

The 2-position branched epoxide (2,2-dialkylepoxide) represented by the formula (1) can be obtained by epoxidizing the vinylidene olefin obtained by the dimerization reaction. The epoxidation reaction can be carried out by using a peroxide. Examples of the peroxide include hydrogen peroxide, an organic peracid, a diacyl peroxide, a ketone peroxide, a hydroperoxide, a dialkyl peroxide, a peroxyketal, an alkyl perester and a percarbonate. These may be used solely or as a mixture of two or more of them. The charging molar ratio of the peroxide and the dimer is preferably peroxide/dimer $\geq 1$, and more preferably $100 \geq$ peroxide/dimer $\geq 1$.

In the case where hydrogen peroxide is used as the peroxide, it can be obtained, for example, through the following reaction. A hydrogen peroxide aqueous solution (hydrogen peroxide content: about 20 to 80% by mass) and a small amount of an acid, such as sulfuric acid and formic acid, are mixed with the vinylidene olefin, and then stirred generally at from 0 to 100° C. for from 1 to 50 hours. The resulting reaction product is poured into water, and an organic layer is washed with water. A hydrogen peroxide aqueous solution (hydrogen peroxide content: about 20 to 80% by mass) and a small amount of an acid, such as sulfuric acid and formic acid, are then again mixed with the organic layer, and the stirring operation is continued at from 0 to 100° C. for from 1 to 50 hours. The organic layer is washed with water and then dried, and the hydrocarbon solvent is distilled off under reduced pressure to obtain the 2-position branched epoxide represented by the general formula (1) as a concentrated liquid.

The 2-position branched epoxide thus obtained is used as a raw material, and the epoxide is subjected to acid rearrangement reaction using a polyacid of a metallic oxoacid as a catalyst, whereby the aldehyde with a 2-position branched long-chain alkyl represented by the general formula (2) can be obtained.

An oxoacid includes an oxoacid containing a non-metallic atom and a metallic oxoacid, and the oxoacid containing a non-metallic atom includes sulfuric acid, sulfurous acid, phosphoric acid, phosphorous acid, hypochlorous acid, chloric acid, perchloric acid, arsenic acid and the like. The metallic oxoacid in the present invention is an acid having a polyhedral structure, such as a tetrahedron, a trigonal pyramid and a octahedron, formed by tetra- to hexa-coordination of a typical metal or a transitional metal with oxygen, and specific examples thereof include silicic acid, aluminic acid, tungstic acid, molybdic acid and vanadic acid. In the present invention, a polyacid of an oxoacid containing a transition metal, such as tungstic acid, molybdic acid and vanadic acid, is preferably used.

As a polyacid, such compounds as pyrophosphoric acid and polyphosphoric acid formed by condensation of phosphoric acid have been known and used widely, and the polyacid of a metallic oxoacid used in the present invention is such a polynuclear complex that contains, as a basic unit, a polyhedron, such as a tetrahedron, a trigonal pyramid and a octahedron, formed by tetra- to hexa-coordination of a typical metal or a transitional metal with oxygen, and is formed by polycondensation of the polyhedrons with edges and apexes thereof being shared, like wooden building blocks. The polynuclear complex is generally referred to as a polyacid, and a Keggin type $(PW_{12}O_{40})^{3-}$ and a Dawson type $(P_2W_{18}O_{62})^{n-}$ are known as typical examples. A polyacid constituted only by a metallic atom and an oxygen atom is an isopolyacid. A heteropolyacid is a polyacid that is constituted by other metals or elements in addition to a typical metal and a transition metal.

In the present invention, a polyacid of tungstic acid, molybdic acid or vanadic acid is preferred as an isopolyacid, and a polyacid of tungstic acid, molybdic acid or vanadic acid with phosphoric acid, silicic acid or boric acid is preferred as a heteropolyacid. Examples of the heteropolyacid include silicotungstic acid and phosphomolybdic acid. In the present invention, particularly, silicotungstic acid, phosphomolybdic acid and the like are preferably used as a heteropolyacid.

In the present invention, the polyacid of a metallic oxoacid may be supported on a carrier. Examples of the carrier that can be used include zirconia, silica, titania and alumina. The polyacid of a metallic oxoacid can be supported according to a known method.

An epoxy compound generally undergoes polymerization easily to provide a polyalkylene ether A 1,2-epoxide of a long-chain α-olefin similarly undergoes polymerization. However, ring-opening reaction of an epoxide using a solvent capable of being reacted with an epoxide brings about solvation. In the case where water is used as a solvent, a 1,2-diol is by-produced. Accordingly, when an epoxide is reacted by using an ordinary acid catalyst with no solvent, dimerization or oligomerization of the epoxide generally proceeds.

However, when a cluster of a metallic oxoacid (oligomer condensate, for example, a heteropolyacid or an isopolyacid) or a polymer thereof (super-high molecular weight condensate, for example, zeolite, silica-alumina) is used, reaction exceeding dimerization (intermolecular reaction) of the epoxide is suppressed, and a product of intramolecular acid rearrangement reaction of the epoxide becomes a main product. In the case where a cluster of a metallic oxoacid (low condensate of an oxoacid containing a transition metal) referred to as a polyacid is used, the catalytic activity and selectivity to a saturated aldehyde with a 2-position branched long-chain alkyl are improved, whereby the target product can be produced with good efficiency.

As by-products, a long-chain alkyl 2-position branched unsaturated alcohol represented by the general formula (i), a long-chain alkyl 2-position branched 1,2-diol represented by the general formula (ii), an epoxide dimer represented by the general formula (iii) and the like are identified, but a 2-position branched unsaturated alcohol, which is an acid rearrangement product having a boiling point close to the aldehyde with a 2-position branched long-chain alkyl represented by the general formula (2) as a target product, is suppressed from being produced, and thus a heteropolyacid is practically useful as the catalyst.

The charging ratio (proportion) of the polyacid of a metallic oxoacid with respect to the vinylidene olefin represented by the general formula (1) is generally from 0.1 to 25 mol of transition metal atoms of the polyacid of a metallic oxoacid used per 1 mol of the vinylidene olefin represented by the general formula (1). For example, it is from 0.1/12 to 25/12 mol for silicotungstic acid $H_4(Si(W_3O_{10})_4) \cdot xH_2O$. In the case where the polyacid of a metallic oxoacid is 0.1 mol or more per transition metallic atoms, the acid rearrangement reaction is accelerated, and in the case where it is 25 mol or less, the polyacid is dissolved through reaction of the polyacid and the epoxide to suppress a phenomenon of suddenly increasing the reaction rate, whereby control of the reaction is facilitated.

The acid rearrangement reaction can be carried out at a reaction temperature of generally about from 20 to 200° C., and preferably from 100 to 150° C., for a reaction time of generally about from 30 minutes to 4 hours, and preferably from 1 to 2 hours. The product obtained through the acid rearrangement reaction can be easily purified by such a method as distillation.

EXAMPLES

The present invention is described in more detail with reference to examples, but the invention is not limited by the examples.

Production Example 1

(1) Dimerization Reaction of Linear α-Olefin 3.0 kg of 1-decene, zirconocene dichloride (metallocene complex, 0.9 g, 3 mmol) and methylaluminoxane (produced by Albemarle Corp., 8 mmol (in terms of Al)) were placed sequentially in a three-neck flask having an internal capacity of 5 L having been substituted with nitrogen, and stirred at room temperature (ca. 20° C.). The reaction solution was changed from yellow to reddish brown. After reacting for 48 hours, 30 mL of methanol was added thereto to terminate the reaction, and 300 mL of a hydrochloric acid aqueous solution was added to the reaction solution, followed by washing the organic layer. The organic layer was then distilled in vacuum to obtain 2.5 kg of a distillate fraction (decene dimer) having a boiling point of 120 to 125° C. at 26.6 Pa (0.2 Torr) Gas chromatography analysis of the distillate fraction revealed that the concentration of the decene dimer was 99% by mass, and the proportion of the vinylidene olefin (2-octyl-1-dodecene) in the dimer was 97% by mass.

(2) Epoxidation Reaction of Vinylidene Olefin 300 g of the decene dimer prepared in the item (1) and mL of toluene were placed in a three-neck flask having an internal capacity of 2 L, and were mixed. While maintaining the temperature of the mixture to 70° C., 150 g of hydrogen peroxide aqueous solution having a concentration of 30% by mass, g of concentrated sulfuric acid and 20 g of formic acid were added thereto. After stirring the mixture at that temperature for 1.5 hours, the reaction mixture was poured into mL of water, followed by washing the organic layer. The organic layer was placed again in the flask, and 150 g of a hydrogen peroxide aqueous solution having a concentration of 30% by mass, 0.5 g of concentrated sulfuric acid and 20 g of formic acid were added thereto. After continuing the stirring operation at 70° C. for 1.5 hours, the mixture was fractionated to obtain an organic layer, which was washed with water and then dried. Toluene as a solvent was distilled off under reduced pressure to obtain 302 g of a concentrated liquid. Analysis of the concentrated liquid by $^1$H-NMR and $^{13}$C-NMR confirmed that the concentrated liquid was 2-octyl-1,2-epoxydodecane with the content thereof being 99%.

Example 1

(1) Acid Rearrangement Reaction with Molybdophosphoric Acid (Heteropoly Acid)

0.5 g of 12 molybdo(IV)phosphoric acid n hydrate (produced by Kanto Chemical Co., Inc.) was charged in a flask having an internal capacity of 300 mL, and while heating the flask to 170° C., water vaporized from the hydrate was removed at a vacuum degree of 133 Pa (1 Torr). The crystals were changed from pale yellow to bluish purple. 100 g (338 mmol) of 2-octyl-1,2-epoxydodecane produced in Production Example 1 was added to 12 molybdo(IV) phosphoric acid having been dehydrated, and stirred at room temperature (25° C.). Heat was generated after lapsing about 10 minutes, and the internal temperature was returned to room temperature after lapsing 30 minutes. The reaction mixture was then heated over an oil bath at 100° C., and heated at that temperature for 2 hours. After cooling, the reaction product was diluted with 100 mL of toluene, and then washed with water to obtain water washing product. Gas chromatography analysis of the product revealed that the formation proportions were 92% by mass for 2-octyl-1-dodecanal, 5% by mass for 1,3-dioxolane as a dimerization product of the epoxide, and 3% by mass for light hydrocarbon compounds. The results are shown in Table 1.

(2) Separation and Purification of 2-Octyl-1-Dodecanal

Toluene was distilled off from the water washing product of the item (1) with an evaporator to obtain 96 g of a concentrated product. The concentrated product was then placed in a vacuum distillation apparatus and distilled at a vacuum degree of 33.3 Pa (0.25 Torr) over an oil bath at 170° C. A distillation fraction of a distillation temperature of from 139 to 145° C. was fractionated to obtain 82 g (277 mmol) of 2-octyl-1-dodecanal. Accordingly, the yield of 2-octyl-1-dodecanal was 82%, and the purity thereof was 97.5%, which revealed that synthesis was attained with high yield and high purity.

(3) Structure of 2-Octyl-1-Dodecanal

The structure of 2-octyl-1-dodecanal purified in the item (2) was identified by $^1$H-NMR and $^{13}$C-NMR. Upon analysis, the carbon atoms of 2-octyl-1-dodecanal were attached with symbols.

As a result of analysis, in $^1$H-NMR, in which the peak of TMS (tetramethylsilane) was designated as 0 ppm, and hydrogen attached to carbon(s) was expressed as (1)H, the attributes of the protons were (1)H 9.55 ppm, (2)H 2.22 ppm, (3)H 1.61 ppm, 1.41 ppm, (4)H-(8)H 1.26 ppm and (9)H 0.88 ppm.

FIG. 1 shows the $^1$H-NMR spectrum.

Figure 2:
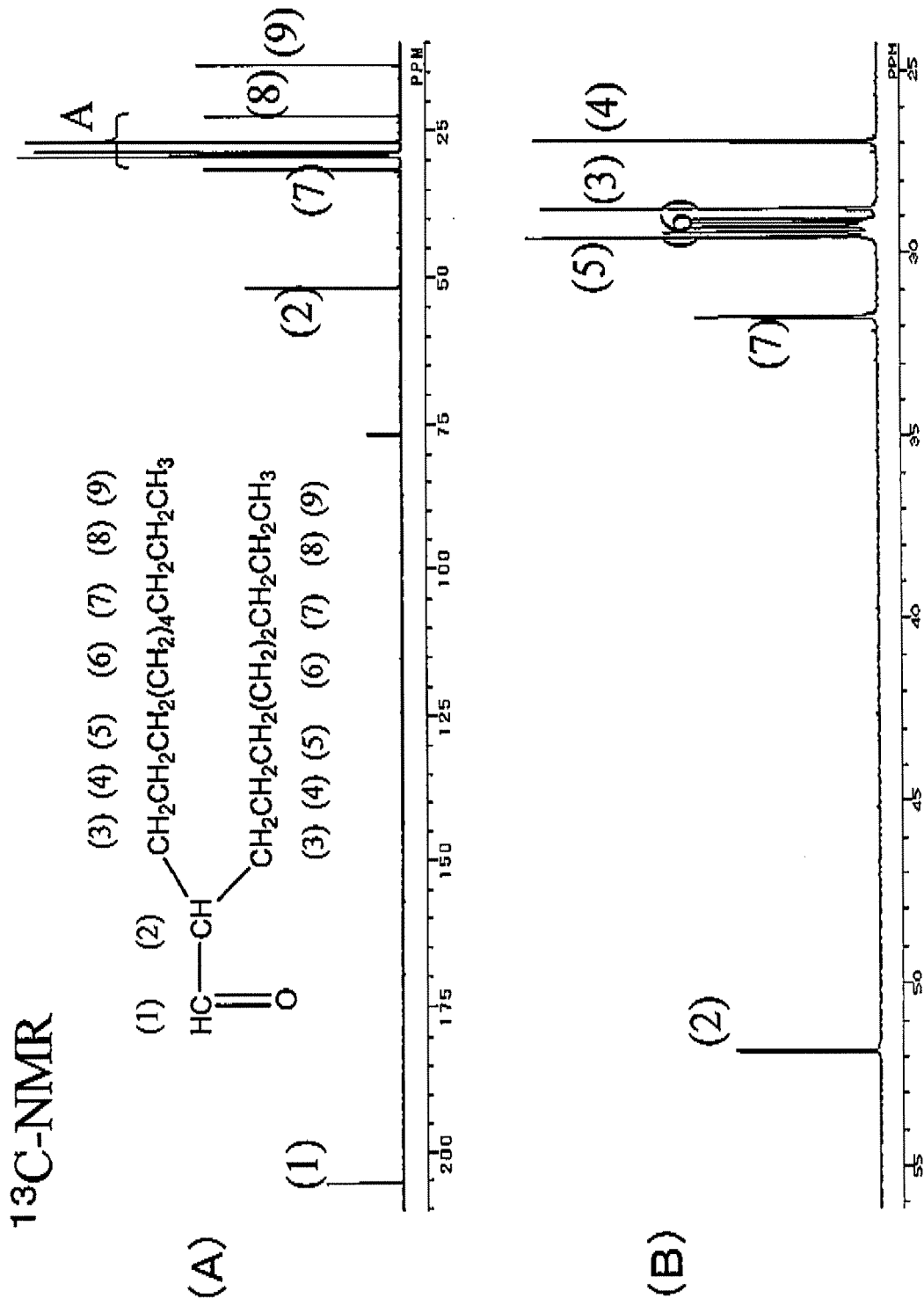
FIG. 2 The figure shows a $^{13}$C-NMR spectrum of 2-octyl-1-dodecanal obtained in Example 1.

In $^{13}$C-NMR, in which the center peak of CDCl$_3$ was designated as 76.91 ppm, the attributes of the carbon were (1) 205.4 ppm, (2) 51.9 ppm, (3) 28.8 ppm, (4) 27.0 ppm, (5) 29.6 ppm, (6) 29.5-29.1 ppm, (7) 31.8 ppm, (8) 22.5 ppm and (9) 13.9 ppm. FIG. 2 shows the $^{13}$C-NMR spectrum. FIG. 2(B) is an enlarged figure of the part shown by a symbol A in FIG. 2(A).

In the $^{13}$C-NMR spectrum, the intensity ratio of the carbon peaks of (2) and (3) is ½, which evidences that there are two atoms of carbon(3) per carbon (2), i.e., a branch of carbon(3) occurs at carbon(2).

Figure 3:
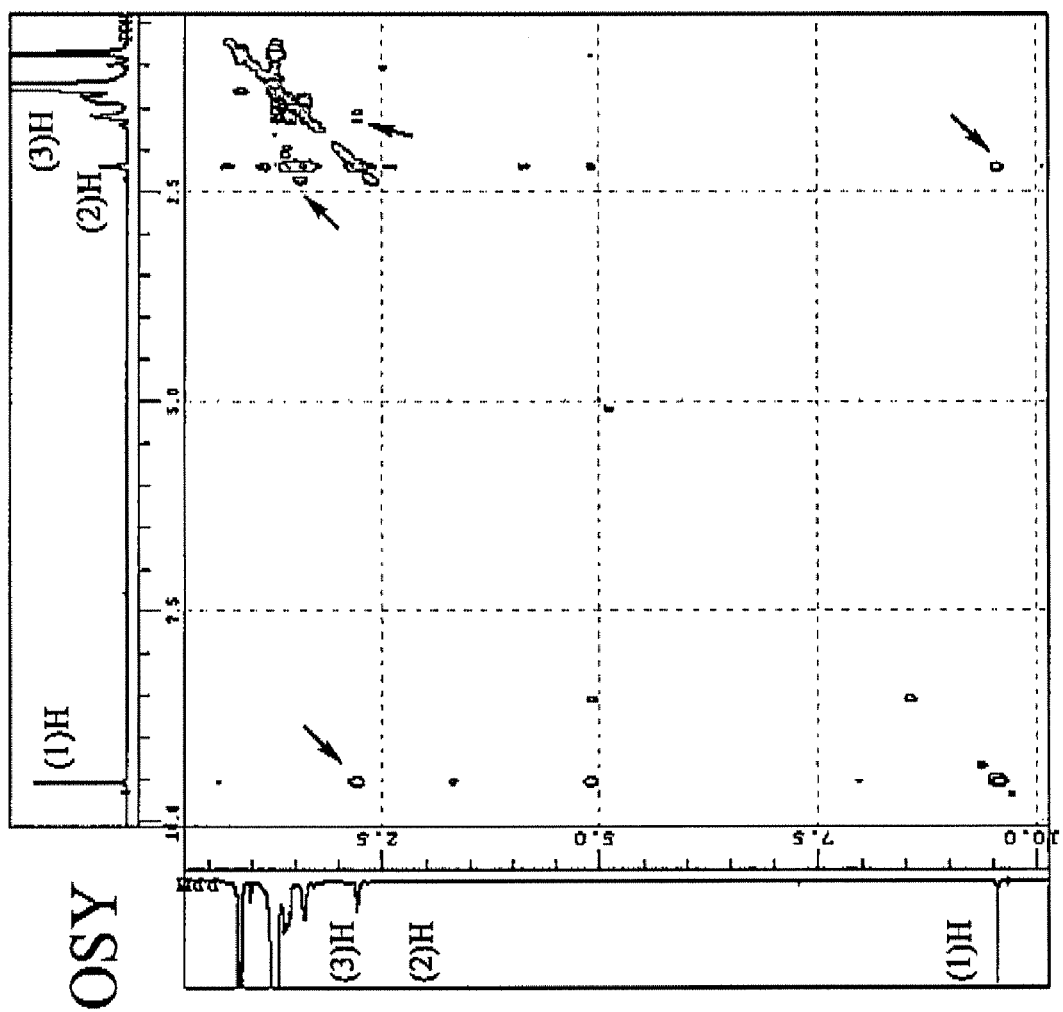
FIG. 3 The figure shows a homonuclear shift correlation (2D-COSY) spectrum of 2-octyl-1-dodecanal obtained in Example 1.

FIG. 3 shows the homonuclear shift correlation (2D-COSY) spectrum. In FIG. 3, correlation signals of (2)H and (1)H, and (2)H and (3)H are observed (shown by arrows in FIG. 3), which indicate the structure. That is, (2)H is positioned between (1)H and (3)H. Furthermore, (1)H is positioned at a low magnetic field, which indicates aldehyde hydrogen.

Example 2

Acid Rearrangement Reaction with Silicotungstic Acid (Heteropoly Acid)

0.05 g of silicotungstic acid hydrate (produced by Kanto Chemical Co., Inc.) was charged in a flask having an internal capacity of 300 mL, and while heating the flask to 170° C., water vaporized from the hydrate was removed at a vacuum degree of 133 Pa (1 Torr). The crystals were changed from white to gray. 100 g (338 mmol) of 2-octyl-1,2-epoxydodecane produced in Production Example 1 was added to silicotungstic acid having been dehydrated, and stirred at room temperature (25° C.). Heat was vigorously generated after lapsing several minutes, and the internal temperature was returned to around room temperature after lapsing 1 hour. The reaction mixture was then heated over an oil bath at 100° C., and heated at that temperature for 1 hour. After cooling, the reaction product was diluted with 100 mL of toluene, and then washed with water to obtain concentrated reaction product. The resulting concentrated reaction product was 96 g. Gas chromatography analysis of the concentrated reaction product revealed that the formation proportions were 72% by mass for 2-octyl-1-dodecanal, 9% by mass for a long-chain alkyl 2-position branched unsaturated alcohol, 4% by mass for a long-chain alkyl 2-position branched 1,2-diol, 9% by mass for 1,3-dioxolane, and 6% by mass for light hydrocarbon compounds. The results are shown in Table 1.

Example 3

Acid Rearrangement Reaction with Molybdic Acid (Isopoly Acid)

0.1 g of hexaammonium heptamolybdate tetrahydrate (produced by Kanto Chemical Co., Inc.) was charged in a Schlenk flask having an internal capacity of 100 mtL, to which 0.1 mL of concentrated sulfuric acid having a concentration of 98% by mass was added, and the mixture was stirred over an oil bath at 80° C. for 30 minutes. 20 g of 2-octyl-1, 2-epoxydodecane was added to the resulting slurry under stirring, and the mixture was stirred continuously at 80° C. for 2 hours. After cooling, the reaction product was diluted with 20 mL of toluene, and then washed with water. Analysis of the reaction product revealed that the formation proportions were 85% by mass for 2-octyl-1-dodecanal, 3% by mass for a long-chain alkyl 2-position branched unsaturated alcohol, 1% by mass for a long-chain alkyl 2-position branched 1,2-diol, 8% by mass for 1,3-dioxolane, and 3% by mass for light hydrocarbon compounds. The results are shown in Table 1.

Example 4

Acid Rearrangement Reaction with Molybdic Acid Supported on Zirconia 9 g of zirconium oxide powder (Zirconia, 3N, produced by Kanto Chemical Co., Inc.), 1 g of phosphomolybdic acid and 50 mL of distilled water were placed on a porcelain dish and then evaporated to dryness under stirring over a water bath. The powder thus obtained was fired in a muffle furnace at 1,073° C. for 2 hours to prepare a molybdic acid/zirconia catalyst. 0.1 g of the powder thus prepared was charged in a Schlenk flask having an internal capacity of 100 mL, to which 20 g of 2-octyl-1,2-epoxydodecane was added, followed by continuing the stirring operation at 100° C. for 2 hours. After cooling, the reaction mixture was diluted with 20 mL of toluene, and the reaction product was filtered and washed with water. Gas chromatography analysis of the reaction product revealed that the formation proportions were 87% by mass for 2-octyl-1-dodecanal, 8% by mass for 1,3-dioxolane, and 5% by mass for light hydrocarbon compounds. The results are shown in Table 1.

Example 5

Acid Rearrangement Reaction with Tungstic Acid Supported on Silica)

0.1 g of 10% by mass silicotungstic acid/silica (N.E. Chemcat Corp.) was charged in a two-neck flask having an internal capacity of 100 mL, to which 20 g of 2-octyl-1,2-epoxydodecane was added, followed by stirring at room temperature for 30 minutes. The reaction mixture was then further stirred over an oil bath at 100° C. for 1 hour. After cooling, the reaction mixture was diluted with 20 mL of toluene, and the reaction product was filtered and washed with water. Gas chromatography analysis of the reaction product revealed that the formation proportions were 77% by mass for 2-octyl-1-dodecanal, 6% by mass for a long-chain alkyl 2-position branched unsaturated alcohol, 2% by mass for a long-chain alkyl 2-position branched 1,2-diol, 8% by mass for 1,3-dioxolane, and 7% by mass for light hydrocarbon compounds. The results are shown in Table 1.

Comparative Example 1

Acid Rearrangement Reaction with Concentrated Sulfuric Acid 1.2 mL of a sulfuric acid aqueous solution having a concentration of 50% by mass and 20 g (67.6 mmol) of 2-octyl-1,2-epoxydodecane were placed in a Schlenk flask having an internal capacity of 100 mL, and continuously stirred at 100° C. for 2 hours. After cooling, the reaction mixture was diluted with 20 mL of toluene, and the reaction product was washed with an alkali aqueous solution. The washed solution was dried with Kyoward 500 (produced by Kyowa Chemical Industry Co., Ltd.) and filtered to obtain 14 g of a concentrated product Gas chromatography analysis of the concentrated product revealed that the formation proportions were 28% by mass for 2-octyl-1-dodecanal, 14% by mass for a long-chain alkyl 2-position branched unsaturated alcohol, 3% by mass for a long-chain alkyl 2-position branched 1,2-diol, 51% by mass for 1,3-dioxolane, and 4% by mass for light hydrocarbon compounds. The results are shown in Table 1.

Comparative Example 2

Acid Rearrangement Reaction with Phosphoric Acid 1.2 mL of 85% by mass phosphoric acid and 20 g of 2-octyl-1,2-epoxydodecane were placed in a Schlenk flask having an internal capacity of 100 mL, and continuously stirred at 100° C. for 2 hours. After cooling, the reaction mixture was diluted with 20 mL of toluene, and the reaction product was washed with an alkali aqueous solution. The washed solution was dried with Kyoward 500 (produced by Kyowa Chemical Industry Co., Ltd.) and filtered to obtain 15 g of a concentrated product. Gas chromatography analysis of the concentrated product revealed that the formation proportions were 23% by mass for 2-octyl-1-dodecanal, 16% by mass for a long-chain alkyl 2-position branched unsaturated alcohol, 4% by mass for a long-chain alkyl 2-position branched 1,2-diol, 40% by mass for 1,3-dioxolane, and 17% by mass for light hydrocarbon compounds. The results are shown in Table 1.

TABLE 1

| | Catalyst | Charged mass ratio catalyst/epoxide | Target product (% by mass) | By-product 1 (% by mass) | By-product 2 (% by mass) | By-product 3 (% by mass) | By-product 4 (% by mass) |
|---|---|---|---|---|---|---|---|
| Example 1 | phosphomolybdic acid | 0.5 g/100 g | 92 | 0 | 0 | 5 | 3 |
| Example 2 | silicotungstic acid | 0.05 g/100 g | 72 | 9 | 4 | 9 | 6 |
| Example 3 | molybdic acid | 0.1 g/20 g | 85 | 3 | 1 | 8 | 3 |
| Example 4 | molybdic acid supported on zirconia | 0.1 g/20 g | 87 | 0 | 0 | 8 | 5 |
| Example 5 | tungstic acid supported on silica | 0.1 g/20 g | 77 | 6 | 2 | 8 | 7 |
| Comparative example 1 | 50% sulfucic acid aqueous solution | 1.2 mL/20 g | 28 | 14 | 3 | 51 | 4 |
| Comparative Example 2 | 85% phosphoric acid | 1.2 mL/20 g | 23 | 16 | 4 | 40 | 17 |

(Note)
Target product: 2-octyl-1-dodecanal
By-product 1: long-chain alkyl 2-position branched unsaturated alcohol
By-product 2: long-chain alkyl 2-position branched 1,2-diol
By-product 3: 1,3-dioxolane (dimer of epoxide)
By-product 4: light hydrocarbon confounds The structure of the by-product 3 was determined as 1,3-dioxolane structure since an antisymmetric stretching $v_{R-O-R}=1,115$ cm$^{-1}$ showing characteristic absorption of ether appeared in the infrared absorption spectrum, and the parent peak 591 ($C_{40}H_{80}O_2=592$) was obtained in the mass spectrum. The structure was also supported by analysis by $^{13}$C-NMR and $^1$H-NMR.

INDUSTRIAL APPLICABILITY

An aldehyde with a 2-position branched long-chain alkyl produced by the production process of the present invention is suitable for an intermediate raw material used in production of a branched alcohol, a branched fatty acid, an aliphatic amine and the like, a resin raw material, such as 1,3-alkanediol and a bisphenol derivative, and a raw material of a functional chemical utilizing a Schiff base and the like.

The invention claimed is:

1. A process for producing an aldehyde with a 2-position branched long-chain alkyl represented by the following general formula (2) comprising: using a 2-position branched epoxide represented by the following general formula (1) as a raw material; and subjecting the epoxide to acid rearrangement reaction with a polyacid of a metallic oxoacid as a catalyst

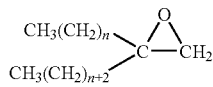 (1)

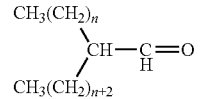 (2)

(In the formulae, n represents an integer of from 5 to 17).

2. The process for producing an aldehyde with a 2-position branched long-chain alkyl as described in claim 1, wherein the 2-position branched epoxide is an epoxidized product of a vinylidene olefin obtained by dimerizing an α-olefin in the presence of a metallocene complex catalyst.

3. The process for producing an aldehyde with a 2-position branched long-chain alkyl as described in claim 1 or 2, wherein in the general formulae (1) and (2), n represents an integer of from 7 to 9.

4. The process for producing an aldehyde with a 2-position branched long-chain alkyl as described in one of claims 1 to 3, wherein the polyacid of a metallic oxoacid is a polyacid containing tungstic acid, molybdic acid or vanadic acid.

5. The process for producing an aldehyde with a 2-position branched long-chain alkyl as described in claim 4, wherein the polyacid containing tungstic acid, molybdic acid or vanadic acid is an isopolyacid that is a polyacid of tungstic acid, molybdic acid or vanadic acid, or a heteropolyacid that is a polyacid of tungstic acid, molybdic acid or vanadic acid with phosphoric acid, silicic acid or boric acid.

* * * * *